United States Patent
Nohara et al.

[11] Patent Number: 6,063,378
[45] Date of Patent: May 16, 2000

[54] THERAPEUTIC AGENT FOR HERNIATED INTERVERTEBRAL DISC

[75] Inventors: Yutaka Nohara, Koshigaya; Hiroki Ishikawa, Kashiwa, both of Japan

[73] Assignee: Seikagaku Corporation, Tokyo, Japan

[21] Appl. No.: 09/137,197

[22] Filed: Aug. 20, 1998

[30] Foreign Application Priority Data

Aug. 22, 1997 [JP] Japan .................................. 9-226872

[51] Int. Cl.⁷ .......................... A61K 38/47; A61K 38/46
[52] U.S. Cl. ................... 424/94.61; 424/94.1; 424/94.6; 424/94.62; 435/200; 435/201; 435/232
[58] Field of Search ................. 424/94.1, 94.6, 424/94.62, 94.61; 435/200, 201, 232

[56] References Cited

U.S. PATENT DOCUMENTS

| | | | |
|---|---|---|---|
| 4,696,816 | 9/1987 | Brown | 424/94.65 |
| 5,496,718 | 3/1996 | Hasimoto et al. | 435/232 |

FOREIGN PATENT DOCUMENTS

| | | |
|---|---|---|
| 576 294 A2 | 12/1993 | European Pat. Off. |
| 0 613 949 A2 | 9/1994 | European Pat. Off. |
| 0 875 253 A2 | 11/1998 | European Pat. Off. |

OTHER PUBLICATIONS

Tsuneto Sugimura, et al., Experimental Chemonucleolysis With Chondroitinase ABC in Monkeys, Spine vol. 21, No. 2 p. 1610165, 1996.

Toyomi Takahashi, et al., Treatment of Canine Intervertebral Disc Displacement With Chondroitinase ABC., Spine vol. 22, No. 13, pp. 1435–1439, 1997.

Comparison of Tissue Reaction with Chondroitinase ABC and Chymopapain in Rabbits as the Basis of Clinical Application in Chemonucleolysis, Fumihiko Kato M.D., et al., Clinical Orthopaedics and Related Research No. 288 Mar. 1993, pp. 294–302.

Chondroitinase ABC (Pharmaceutical Grade) for Chemonucleolysis, Kjell Olmarker, MD. PhD. et al., Spine, vol. 21, No. 17, 1996, pp. 1952–1956.

*Primary Examiner*—Leon B. Lankford, Jr.
*Attorney, Agent, or Firm*—Knobbe, Martens, Olson & Bear, LLP

[57] ABSTRACT

A pharmaceutical composition and an agent that can be used for treatment of epidurally migrating herniated intervertebral disc are provided. The composition comprises a glycosaminoglycan degrading enzyme, preferably chondroitinase, more preferably chondroitinase ABC, in an amount effective to dissolve nucleus pulposus epidurally existing.

15 Claims, 1 Drawing Sheet

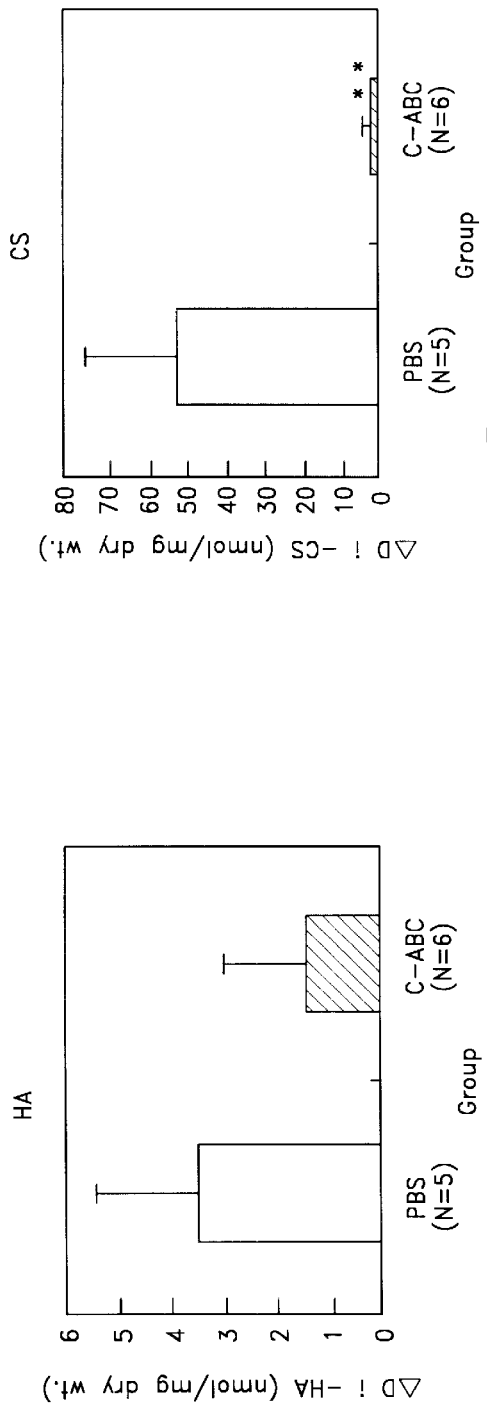
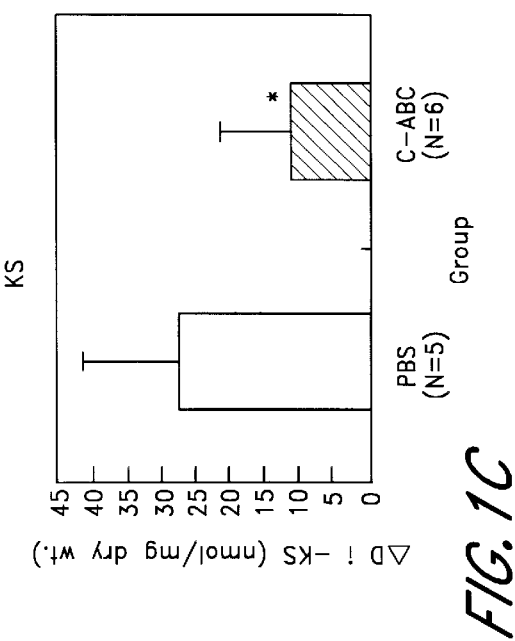
FIG. 1A
FIG. 1B
FIG. 1C

THERAPEUTIC AGENT FOR HERNIATED INTERVERTEBRAL DISC

TECHNICAL FIELD

The present invention belongs to the field of the art relating to medical use of glycosaminoglycan degrading enzymes. More specifically, the invention relates to a pharmaceutical composition for administration to the vertebral epidural space comprising a glycosaminoglycan degrading enzyme and a pharmaceutical carrier and a therapeutic agent for epidurally migrating herniated intervertebral disc comprising a glycosaminoglycan degrading enzyme as an active ingredient.

BACKGROUND ART

Herniated intervertebral disc is a disease attributed to protrusion of nucleus pulposus of an intervertebral disc. The protruded nucleus pulposus stimulates nerves therearound to cause symptoms including lower back pain.

Among herniated intervertebral disc, herniated intervertebral disc classified into sequestered type herniated intervertebral disc according to Macnab's classification is herniated intervertebral disc where nucleus pulposus of an intervertebral disc protrudes through the most outer layer of anulus fibrosus and posterior mediastinal ligaments to completely separate from a central intervertebral disc and migrates into the vertebral epidural space in the vertebral canals. Sequestered type herniated intervertebral disc spontaneously disappears a certain period of time. However, it causes severe pain until its spontaneous disappearance and the patients suffer from considerable pain. Thus, it has been desired to treat them so as to save them from such severe pain as soon as possible.

On the other hand, among herniated intervertebral disc, herniated intervertebral disc classified into transligamentous extrusion type herniated intervertebral disc according to Macnab's classification is herniated intervertebral disc where nucleus pulposus of an intervertebral disc protrudes through the most outer layer of anulus fibrosus and posterior mediastinal ligaments such as that in sequestered type herniated intervertebral disc but it does not separate from a central intervertebral disc. Thus, since transligamentous extrusion type herniated intervertebral disc is characterized by existence of epidurally nucleus pulposus in common with sequestered type herniated intervertebral disc, it has been desired to treat patients of transligamentous extrusion type herniated intervertebral disc with the same manner for treating patients of sequestered type herniated intervertebral disc. In the present specification, herniated intervertebral disc where nucleus pulposus is existing epidurally, such as transligamentous extrusion type herniated intervertebral disc and sequestered type herniated intervertebral disc, is generally called as "epidurally migrating herniated intervertebral discs".

For the conventional treatment of herniated intervertebral disc, intervertebral disc dissolution treating method (ID method) was developed in which proteolytic enzyme such as chymopapain or bacterial collagenase is injected into the intervertebral disc of a patient with hernia to dissolve the herniated part. Chymopapain (trade name: Chymodiactin) is commercially available as a drug.

By the above ID method using proteolytic enzyme, however, the protein portions of the surrounding structural tissue are dissolved as well as the herniated part of the spine and intervertebral disc. Thus, this method is disadvantageous in likely causing side effects such as neuroparalysis or onset of allergy.

Particularly, when the above-described proteolvtic enzyme is injected into the vertebral epidural space to dissolve nucleus pulposus migrating in the vertebral epidural space, the proteolytic enzyme dissolves not only the nucleus pulposus but also spine. Thus, such administration and treatment are not acceptable.

Recently, an attempt has been made to treat herniated intervertebral disc by injecting chondroitinase ABC or chondroitinase AC into the intervertebral disc. Thus, it has been expected to use these enzymes as a therapeutic drug for herniated intervertebral disc (U.S. Pat. No. 4,696,816 Specification, Clinical Orthopaedics, 253, 301–308 (1990)).

For example, chondroitinase ABC [EC 4.2.2.4] is an enzyme that degrades glycosaminoglycan to unsaturated oligosaccharide and unsaturated disaccharide. It strongly catalyzes degradation of chondroitin sulfate A derived from mammalian cartilage, chondroitin sulfate C derived from cartilage of shark, and chondroitin sulfate B which is called dermatan sulfate derived from mammalian skin, whereas it weakly catalyzes degradation of hyaluronan.

Chondroitinase as described above has been conventionally directly injected into the intervertebral disc. However, such administration is not effective for treating epidurally migrating herniated intervertebral disc. This is because injection of chondroitinase into the intervertebral disc cannot dissolve nucleus pulposus migrating in the vertebral epidural space.

Any composition for administration of a glycosaminoglycan degrading enzyme such as chondroitinase to the vertebral epidural space has not been known so far. Also, any therapeutic agent for epidurally migrating herniated intervertebral disc comprising a glycosaminoglycan degrading enzyme like chondroitinase as an active ingredient has not been known.

Therefore, it has been desired to develop a pharmaceutical composition and an agent that can be used for treating epidurally migrating herniated intervertebral disc.

DISCLOSURE OF THE INVENTION

An object of the present invention is to provide a pharmaceutical composition for administration to the vertebral epidural space for the treatment as described above and a therapeutic agent for epidurally migrating herniated intervertebral disc.

As a result of intensive investigation to achieve the above object, the present inventors have found that nucleus pulposus in the vertebral epidural space is remarkably dissolved without affecting spinal cord by administering a glycosaminoglycan degrading enzyme to the vertebral epidural space and succeeded in providing a pharmaceutical composition and a therapeutic agent for use in the above administering it, thereby completing the present invention.

The present invention provides a pharmaceutical composition for administration to a vertebral epidural space, comprising a glycosaminoglycan degrading enzyme and a pharmaceutical carrier (hereinafter simply referred to as "the composition of the present invention") and a therapeutic agent for epidurally migrating herniated intervertebral disc comprising a glycosaminoglycan degrading enzyme as an active ingredient (hereinafter simply referred to as "the therapeutic agent of the present invention").

The mode for carrying out the present invention will be illustrated below.

[1] The Composition of the Present Invention

The composition of the present invention is a pharmaceutical composition for administration to a vertebral epidural space, comprising a glycosaminoglycan degrading enzyme and a pharmaceutical carrier. The glycosaminoglycan degrading enzyme and the pharmaceutical carrier that can be used in the present invention will be described in detail below.

(1) Glycosaminoglycan Degrading Enzyme

Glycosaminoglycan degrading enzymes that can be used in the composition of the present invention are not particularly restricted as long as they are capable of degrading one or two or more of glycosaminoglycans contained in nucleus pulposus. Preferred are those capable of degrading chondroitin sulfate called chondroitinase or keratan sulfate called keratanase. Particularly, chondroitinase is more preferably used.

Any enzyme that degrades chondroitin sulfate can be used as chondroitinase to be used in the composition of the present invention. Specific examples of known chondroitinases include chondroitinase ABC (derived from *Proteus vulgaris*; Japanese Patent Application Laid-open No 6-153947, T. Yamagata, H. Saito, O. Habuchi, and S. Suzuki, J. Biol. Chem., 243, 1523 (1968), S. Suzuki, H. Saito, T. Yamagata, K. Anno, N. Seno, Y. Kawai, and T. Furuhashi, J. Biol. Chem., 243, 1543 (1968)), chondroitinase AC (derived from *Flavobacterium heparinum*; T. Yamagata, H. Saito, O. Habuchi, and S. Suzuki, J. Biol. Chem., 243, 1523 (1968)), chondroitinase ACII (derived from *Arthrobacter aurescens*; K. Hiyama, and S. Okada, J. Biol. Chem., 250, 1824 (1975), K. Hiyama and S. Okada, J. Biochem. (Tokyo), 80, 1201 (1976)), chondroitinase ACIII (derived from Flavobacterium sp. Hp102; Hirofumi Miyazono, Hiroshi Kikuchi, Keiichi Yoshida, Kiyoshi Morikawa, and Kiyochika Tokuyasu, Seikagaku, 61, 1023 (1989)), chondroitinase B (derived from *Flavobacterium heparinum*; Y. M. Michelacci and C. P. Dietrich , Biochem. Biophys. Pes. Commun., 56, 973 (1974), Y. M. Michelacci and C. P. Dietrich, Biochem. J., 151, 121 (1975), Kenichi Maeyama, Akira Tawada, Akiko Ueno, and Keiichi Yoshida, Seikagaku, 57, 1189 (1985)), chondroitinase C (derived from Flavobacterium sp. Hp102; Hirofumi Miyazono, Hiroshi Kikuchi, Kelichi Yoshida, Kiyoshi Morikawa, and Kiyochika Tokuyasu, Seikagaku, 61, 1023 (1939)), and the like. Any of these chondroitinases can be used. It is also possible to use such chondroitinases as chondroitin sulfate degrading enzyme derived from human as described in Japanese Patent Application Laid-coen No 9-168384 and chondroitin sulfate ABC exolyase (A. Hamai, N. Hashimoto, H. Mochizuki, F. Kato, Y. Makiguchi, K. Horie, and S. Suzuki, J. Biol. Chem., 272, 9123–9130 (1997).

Each of these chondroitinases are mere examples and chondroitinases that can be used in the composition of the present invention are not limited thereto. The chondroitinase to be used in the composition of the present invention may be one or a mixture of plural chondroitinases. The term "chondroitinase" simply referred to herein has both of the above meanings.

Specific examples of known keratanases that can be used in the composition of the present invention include endo-β-galactosidase derived from *Escherichia freundii* (H. Nakagawa, T. Yamada, J-L. Chien, A. Gardas, M. Kitamikado, S-C. Li, and Y-T. Li, J. Biol. Chem., 255, 5955 (1980)), endo-β-galactosidase derived from Pseudomonas sp. IFO-13309 strain (K. Nakazawa, N. Suzuki, and S. Suzuki, J. Biol. Chem., 250, 905 (1975), K. Nakazawa and S. Suzuki, J. Biol. Chem., 250, 912 (1975)), endo-β-galactosidase produced by *Pseudomonas reptilivora* as described in Japanese Published Examined Patent Application No 57-41236, endo-β-N-acetylglucosaminidase derived from Bacillus sp. Ks36 (Shinichi Hashimoto, Kiyoshi Morikawa, Hiroshi Kikuchi, Keiichi Yoshida, and Kiyochika Tokuyasu, Seikagaku, 60, 935 (1988)), endo-β-N-acetylglucosaminidase derived from *Bacillus circulans* KsT202 (described in WO96/16166), and the like. Any of these keratanases can be used in the composition of the present invention.

Each of these keratanases are mere examples and the keratanases that can be used in the composition of the present invention are not limited thereto. The keratanase to be used in the composition of the present invention may be one or a mixture of plural keratanases. The term "keratanase" simply referred to herein has both of the above meanings.

As the glycosaminoglycan degrading enzymes to be used in the composition of the present invention, it is extremely preferable to use chondroitinase ABC. Among chondroitinase ABC, it is preferable to use chondroitinase ABC derived from *Proteus vulgaris*.

The glycosaminoglycan degrading enzymes to be used in the composition of the present invention are preferably enzymes that are purified to the medically applicable level and do not substantially contain any medically unacceptable contaminants. For example, when chondroitinase is used as the glycosaminoglycan degrading enzyme, the enzyme is preferably purified to show enzymatic specific activity of not less than 300 U/mg protein. More preferably, the enzyme is purified to show enzymatic specific activity of not less than 300 U/mg protein, to substantially contain no endotoxin, and to contain nucleic acids and proteases in amounts not more than the respective detection limits. Purified chondroitinase ABC having such properties are particularly preferred.

One unit (1 U) of the glycosaminoglycan degrading enzyme used herein is defined as the amount of enzyme liberating 1 micromole of the reaction product from glycosaminoglycan per minute under the conditions of the optimal pH and the optimal temperature. The definition of 1 U of various glycosaminoglycan degrading enzymes are described below.

One unit of chondroitinase ABC is defined as the amount of enzyme liberating 1 micromole of unsaturated disaccharide from chondroitin 6-sulfate per minute at pH 8.0 and at 37° C.

One unit of chondroitinase AC (derived from *Flavobacterium heparinum*) is defined as the amount of enzyme liberating 1 micromole of unsaturated disaccharide from chondroitin 6-sulfate per minute at pH 7.3 and at 37° C.

One unit of chondroitinase ACII (derived from *Arthrobacter aurescens*) is defined as the amount of enzyme liberating 1 micromole of unsaturated disaccharide from chondroitin 6-sulfate per minute at pH 6.0 and at 37° C.

One unit of chondroitinase B (derived from *Flavobacterium heparinum*) is defined as the amount of enzyme liberating a UV-absorbing substance equimolar to 1 micromole of a hexuronic acid residue from dermatan sulfate per minute at pH 8.0 and at 30° C.

One unit of endo-β-galactosidase derived from *Escherichia freundii* is defined as the amount of enzyme liberating a reducing group equimolar to 1 micromole of galactose from keratan sulfate per minute at pH 5.8 and at 37° C.

One unit of endo-β-galactosidase derived from Pseudomonas sp. IFO-13309 strain is defined as the amount of enzyme liberating a reducing group equimolar to 1 micromole of galactose from keratan sulfate per minute at pH 7.4 and at 37° C.

One unit of endo-β-N-acetylglucosaminidase derived from Bacillus sp. Ks36 is defined as the amount of enzyme liberating a reducing group equimolar to 1 micromole of N-acetylglucosamine from keratan sulfate per minute at pH 6.5 and at 37° C.

For example, when chondroitinase ABC having enzymatic specific activity of not less than 300 U/mg protein is used, proteoglycan at the targeted part, for example, the vertebral epidural space of epidurally migrating herniated intervertebral disc, can be appropriately degraded without affecting tissues around the targeted part by administering it to a living body as an injectable pharmaceutical preparation. Thus, the enzyme can be a safe and effective medicine. Such chondroitinase ABC can be obtained by, for example, the method as described in Japanese Patent Application Laid-open No 6-153947.

In the composition of the present invention, it is possible to use one glycosaminoglycan degrading enzyme or a mixture of plural glycosaminoglycan degrading enzymes. For example, a mixture of one or two or more of chondroitinases and one or two or more of keratanases can be used in the composition of the present invention.

The composition of the present invention preferably contains such glycosaminoglycan degrading enzymes in an amount effective to dissolve epidurally existing nucleus pulposus in a state of separated, extruded, or the like. The term "amount effective" used herein means the amount effective to dissolve nucleus pulposus existing in the vertebral epidural space so as to obviate its influence. Such an amount varies depending on symptom, age, and the like of patients. Though it is not particularly limited as long as it can dissolve epidurally existing nucleus pulposus and obviate its influence, it is preferably not less than 5 U, more preferably 5 to 400 U, and further preferably 5 to 200 U, in terms of a dose to be normally given to a part at a time contained in the composition of the present invention.

Further, the composition of the present invention may contain, in addition to the glycosaminoglycan degrading enzymes, a substance capable of dissolving nucleus pulposus different from the glycosaminoglycan degrading enzyme as an active ingredient. The "substance capable of dissolving nucleus pulposus different from the glycosaminoglycan degrading enzyme" used herein is not particularly limited as long as it does not cause serious side effects when formulated together with the glycosaminoglycan degrading enzyme or administered in combination with the enzyme, or one of the substance and the enzyme does not inhibit the nucleus pulposus-dissolving effect that the other inherently possesses. To be noted, the composition of the present invention should not be formulated or administered together with proteolytic enzyme that degrades spinal cord because the composition of the present invention is administered into the vertebral epidural space.

(2) Pharmaceutical Carrier

The pharmaceutical carriers to be used in the composition of the present invention are the pharmaceutically acceptable carriers and include commonly used excipient, binders, lubricants, colorants, disintegrating agents, buffering agents, isotonizing agents, preservatives, anesthetics, and the like components usually used for medicines.

The pharmaceutical carriers to be used in the composition of the present invention are preferably those containing reducing impurities in an amount per gram of a pharmaceutical carrier of not more than 0.4 mL, particularly not more than 0.36 mL, when it is measured by titration using ammonium cerium nitrate. More preferably, the pharmaceutical carriers contain peroxides in a concentration of not more than 20 ppm, particularly not more than 18.5 ppm. Because of having such properties, when the composition of the present invention is provided in the form of a lyophilized product, it becomes possible to minimize the decrease of enzymatic activity of the glycosaminoglycan degrading enzyme before and after lyophilization. Further, if the composition is preserved at ordinary temperature for a long time, the decrease of enzymatic activity of the glycosaminoglycan degrading enzyme can be minimized. For example, when the composition is preserved in a glass container charged with nitrogen gas at 40° C. for 30 days, it is possible to retain not less than 90% of enzymatic activity of the glycosaminoglycan degrading enzyme compared with that at the time of initiation of preservation.

The enzymatic activity of the glycosaminoglycan degrading enzyme can be measured by the known methods. For example, it can be determined by reacting the glycosaminoglycan degrading enzyme with glycosaminoglycan as a substrate and measuring absorbance of disaccharide thus produced.

The amount of reducing impurities in the pharmaceutical carrier can be measured by titration using ammonium cerium nitrate. The "titration using ammonium cerium nitrate" means the method that comprises dissolving 2 g of the pharmaceutical carrier in 25 mL of warm water, adding thereto 25 mL of dilute sulfuric acid and 0.1 mL of ferroin, namely tris(1,10-phenanthroline)iron (II) complex: [Fe$(C_{12}H_8N_2)_3$]$^{2+}$, and titrating the solution with 0.01N of ammonium cerium nitrate until blue green color of the solution changed from red is maintained for 30 seconds.

The concentration of peroxide in the pharmaceutical carrier can be determined by accurately weighing 1 g of the pharmaceutical carrier, adding distilled water thereto to make 10 mL, namely making a 10% (w/v) aqueous solution, adding to 0.8 mL of this solution 0.25 mL of 20% (v/v) sulfuric acid aqueous solution and 0.15 mL of 1M $TiSO_4$ (manufactured by BDH), measuring ultraviolet absorption at 408 nm, and calculating $H_2O_2$ concentration based on a calibration curve prepared by using predetermined concentrations of $H_2O_2$.

When the amount of reducing impurities and/or the concentration of peroxide in the pharmaceutical carrier to be desirably used in the composition of the present invention exceed(s) the limit as defined above or the values are required to be reduced to lower than the desired level, the amount of reducing impurities and the concentration of peroxide can be reduced by, for example, treating the pharmaceutical carrier with activated carbon by the method commonly used. The concentration of peroxide can also be reduced by heat treatment of the pharmaceutical carrier.

Specific examples of the pharmaceutical carrier that can be used in the present invention include, dextrans, saccharose, lactose, maltose, xylose, trehalose, mannitol, xylitol, sorbitol, inositol, serum albumin, gelatin, creatinine, polyethylene glycol, nonionic surface active agent (e.g., polyoxyethylene sorbitan fatty acid ester, polyoxyethylene hydrogenated castor oil, sucrose fatty acid ester, polyoxyethylene polyoxypropylene glycol), and the like.

Examples of polyoxyethylene sorbitan fatty acid esters referred to as polysorbate include monolaurate, monopalmitate, monooleate, monostearate, triorate, and the like esters of polyoxyethylene sorbitan, wherein degree of polymerization of ethylene oxide is about 20. Commercially available products thereof are polysorbate 80 which is polyoxyethylene sorbitan monooleate (20 E.O.), polysorbate 60 which is polyoxyethylene sorbitan monostearate (20 E.O.), polysorbate 40 which is polyoxyethylene sorbitan monopalmitate (20 E.O.), polysorbate 20 which is polyoxyethylene sorbitan monolaurate (20 E.O.), polysorbate 21, 81, 65, 85, and the like, wherein 20 E.O. means degree of polymerization of ethyleneoxide of the polyoxyethylene portion is about 20. Polyoxyethylene hydrogenated castor oil is exemplified by commercially available products such as HCO-10, HCO-50, HCO-60 (Nikko Chemicals Co., Ltd.), and the like. Sucrose fatty acid ester includes commercially available products such as DK Ester F-160 (Daiichi Kogyo Seiyaku Co., Ltd.), Ryoto Sugar Ester (Mitsubishi Kagaku Foods), and the like. Polyoxyethylene polyoxypropylene glycol referred to as poloxamer includes a commercially available product such as Pluronic F-68 (Asahi Denka Kogyo K.K.), and the like.

The buffering agent is not particularly limited as long as it is physiologically acceptable, such as a buffering agent containing one or more components selected from hydrochloric acid, sodium hydroxide, sodium carbonate, sodium hydrogencarbonate, phosphoric acid, potassium dihydrogenphosphate, dipotassium hydrogenphosphate, sodium dihydrogenphosphate, disodium hydrogenphosphate, aminoacetic acid, sodium benzoate, citric acid, sodium citrate, acetic acid, sodium acetate, tartaric acid, sodium tartrate, lactic acid, sodium lactate, ethanolamine, arginine, ethylenediamine, and the like.

Preferably, the pharmaceutical carrier to be used in the composition of the present invention has purity at the pharmaceutically applicable level and does not substantially contain substances that are not acceptable to be contaminated in medicines.

In the composition of the present invention, these pharmaceutical carriers may be used in combination. It is preferable to use either polyethylene glycol or saccharose or a mixture of these compounds, or polyoxyethylene sorbitan fatty acid ester, particularly polyoxyethylene sorbitan monooleate (20 E.O.).

When the composition of the present invention is provided in the lyophilized form, a mixture of polyethylene glycol and saccharose is particularly preferably used because it shows such effects as preventing the decrease of enzymatic activity of the glycosaminoglycan degrading enzyme after lyophilization, keeping low water content in the lyophilized product. Further, a solution of the lyophilized product is clear and free from foreign substances and the decrease of enzymatic activity of the glycosaminoglycan degrading enzyme is small when the lyophilized product is preserved for a long time.

In this occasion, polyethylene glycol to be used is preferably one containing reducing impurities in an amount per gram of polyethylene glycol of not more than 0.4 mL, particularly not more than 0.36 mL, when it is measured by titration using ammonium cerium nitrate. It is more preferable to use polyethylene glycol containing peroxides in a concentration of not more than 20 ppm, particularly not more than 18.5 ppm, per gram of polyethylene glycol.

Polyethylene glycol to be used preferably has average molecular weight of 200 to 25,000. More preferably, it is solid at ordinary temperature. For example, its average molecular weight is more preferably 2,000 to 9,000, particularly preferably 2,000 to 4,000, and most preferably 3,000 to 4,000. Polyethylene glycol having average molecular weight of 3,000 to 4,000 include, for example, those having average molecular weight of 3,250, 3,350, and 4,000.

Saccharose to be used together with polyethylene glycol is preferably one containing reducing impurities in an amount per gram of saccharose of not more than 0.4 mL, particularly not more than 0.36 mL, when it is measured by titration using ammonium cerium nitrate. It is more preferable to use saccharose containing peroxides in a concentration of not more than 20 ppm, particularly not more than 18.5 ppm, per gram of saccharose.

Since commercially available saccharose generally contains endotoxin at a high level, it is preferable to treat it with activated carbon or the like so as to make the endotoxin concentration in a 10% (w/w) saccharose solution not more than 0.03 EU/mL, desirably not more than 0.01 EU/mL, more desirably not more than 0.006 EU/mL.

The endotoxin concentration in saccharose can be measured by the known endotoxin-measuring method. It is preferable to use the limulus test using limulus amebocyte lysate component. An endotoxin-specific limulus reagent is preferred as a limulus reagent used in the limulus test. As the limulus reagent, the following commercially available limulus reagents can be used; Toxicolor systems LS-6, LS-20, and LS-200, Endospecy ES-6, Endospecy ES-200 (these products are available from Seikagaku Corporation), Limulus ES-II Test Wako, Limulus ES-II Single Test Wako, Limulus ES-III Test Wako, Limulus ES-J Test Wako (these products are available from Wako Pure Chemical Industries).

When a mixture of polyethylene glycol and saccharose is used as the pharmaceutical carrier, the mixture preferably contains reducing impurities in an amount per gram of the mixture of not more than 0.4 mL, particularly not more than 0.36 mL, when it is measured by titration using ammonium cerium nitrate. More preferably, the concentration of peroxides per gram of the mixture of polyethylene glycol and saccharose is not more than 20 ppm, particularly not more than 18.5 ppm.

When polyoxyethylene sorbitan fatty acid ester is used as the pharmaceutical carrier, it is preferable to use the ester containing reducing impurities in an amount per gram thereof of not more than 0.4 mL, particularly not more than 0.36 mL, when it is measured by titration using ammonium cerium nitrate. It is more preferable to use the ester having the concentration of peroxides per gram thereof is not more than 20 ppm, particularly not more than 18.5 ppm.

When a mixture of polyethylene glycol and saccharose is used as the pharmaceutical carrier, a weight ratio of polyethylene glycol/saccharose is generally adjusted to about 0/1 to 10/1, particularly preferably about 2/1.

The isotonizing agent includes salts such as sodium chloride, saccharides, and the like.

Though the mixing ratio of the glycosaminoglycan degrading enzyme and the pharmaceutical carrier is not particularly limited, one of ordinary skill in the art would appropriately determine the mixing ratio based on the dose, or the formulation of the composition of the present invention. For example, in the case that the composition of the present invention is provided or preserved in the lyophilized form, the content of the glycosaminoglycan degrading enzyme in the composition of the present invention is preferably at such a level as to keep the shape of the lyophilized cake.

The composition of the present invention can be prepared using the glycosaminoglycan degrading enzyme and the above-described pharmaceutical carrier in accordance with the known pharmaceutical methods. The composition of the present invention may be in the solution, frozen, or dehydrated form.

Among these forms, the composition of the present invention is preferably in the form of dehydrate, more preferably lyophilization, or lyophilizate.

When the composition of the present invention is provided as lyophilizate, the water content in the lyophilizate of the composition of the present invention is preferably not more than 3% (w/w) since it is considered that lyophilized preparations having lower water content shows higher stability and the water content of lyophilized preparations is usually adjusted to not more than 3% (w/w) from the pharmaceutical viewpoint. The water content can be measured by, for example, dry reducing weight method (TG method) that is carried out by heating a sample under the conditions which comprises the steps of heating a sample from 25° C. up to 105° C. at the rate of 2.5° C./min and, when the temperature reaches 105° C., keeping it at that temperature for 20 min, weighing the sample with a microbalance before and after heating, thereby determining the lost weight as the water content. Alternatively, the water content can be measured by Karl Fisher method that is carried out by stirring a sample in methanol for 3 min, extracting water, subjecting the extracted water to coulometric titration, and calculating the water content based on the required quantity of electricity (C:coulomb).

When the composition of the present invention provided as lyophilizate is dissolved in physiological saline, the solution is preferably clear and free from foreign materials. It is easily determined by observation with naked eyes whether the solution is clear and free from foreign materials.

When the composition of the present invention is in the solution form; in the case that the composition of the present invention is provided as the frozen form, the composition can be in the solution form before freezing and after thawing and, in the case that the composition of the present invention is provided as a lyophilizate, it can be in the solution form before lyophilization and after dissolution by adding a solvent, it is desirable to adjust the pH to usually 5 to 9, preferably 6 to 8. For this purpose, a buffering agent capable of keeping the above pH range is usually added to the composition of the present invention. Such a buffering agent is not particularly limited as long as it is physiologically acceptable, including, for example, hydrochloric acid, sodium hydroxide, sodium carbonate, sodium hydrogencarbonate, phosphoric acid, potassium dihydrogenphosphate, dipotassium hydrogenphosphate, sodium dihydrogenphosphate, disodium hydrogenhosphate, aminoacetic acid, sodium benzoate, citric acid, sodium citrate, acetic acid, sodium acetate, tartaric acid, sodium tartrate, lactic acid, sodium lactate, ethanolamine, arginine, ethylenediamine, and a mixture thereof. A phosphate buffer or buffering agent is particularly preferred. The solution form of the composition of the present invention can be adjusted and kept to have the pH range from 5 to 9, preferably 6 to 8, using the above-described buffering agents. If the pH is lower than 5 or higher than 9, the glycosaminoglycan degrading enzyme may possibly be deactivated or generate insoluble matter in the solution form. The concentration of the buffering agent contained in the composition of the present invention is not less than 1 mM, preferably 10 to 50 mM, in the solution form. The composition of the present invention may contain, in addition to the buffering agent, a component necessary for isotonization (salts such as sodium chloride, saccharides, etc.), a preservative, anesthetic, and the like.

The composition of the present invention can be, as it is, a final dosage form to be administered as a medicine. It can also be used as a material for other final dosage forms, for example, liquid preparations, lyophilized preparations, and the like.

The composition of the present invention can be used mainly as a preparation for injection containing the glycosaminoglycan degrading enzyme as an active ingredient. When the composition of the present invention is provided as a liquid preparation for injection, the liquid composition of the present invention produced by the above-described method is put into ampules, vials, syringes for injection, and the like appropriate containers, which are then sealed to be distributed as they are or to be preserved to serve as injections.

When the composition of the present invention is provided as a frozen preparation for injection, the frozen composition of the present invention produced as described above is retained in a sealed state in ampules, vials, syringes for injection, and the like appropriate containers, which are distributed or preserved and melted before administration to serve as injections.

When the composition of the present invention is provided as a dry preparation for injection, the dry composition of the present invention produced as described above is retained in a sealed state in ampules, vials, syringes for injection, and the like appropriate containers, which are distributed or preserved and dissolved in distilled water for injection, physiological saline, a glucose aqueous solution, a sorbitol aqueous solution, and the like to serve as injections. The dry composition of the prevent invention can be provided in combination with a solvent for dissolving the composition.

Among the preparations for injection as described above, the dry composition is preferred and the lyophilized composition is more preferred. Namely, the composition of the present invention is particularly preferably in the form of a lyophilized preparation for injection.

The composition of the present invention can be administered as an injection to vertebral epidural space. Since the composition of the present invention is particularly useful for treatment of epidurally migrating herniated intervertebral disc, it is preferably administered to the vertebral epidural space of epidurally migrating herniated intervertebral disc.

Since the composition of the present invention is useful for treatment of herniated intervertebral disc classified into "sequestered type" and that classified into "transligamentous extrusion type" according to Macnab's classification, it can be administered to the vertebral epidural space of these types of herniated intervertebral disc.

Its dose should be determined independently depending on symptoms, ages, and the like of a patient and is not particularly limited. For example, when chondroitinase ABC is used as the glycosaminoglycan degrading enzyme and administered to a certain part, about 5 to 200 U of the enzyme can be administered per dose.

The composition of the present invention can be administered to the vertebral epidural space in the case of epidurally migrating herniated intervertebral disc of vertebrate animals, particularly mammals, that may possibly suffer from epidurally migrating herniated intervertebral disc. Preferably, the composition can be the one for administration to the vertebral epidural space in the case of sequestered type or transligamentous extrusion type herniated intervertebral disc of human.

[2] Therapeutic Agent of the Present Invention

The therapeutic agent of the present invention is a therapeutic agent for epidurally migrating herniated intervertebral disc which is characterized by existence of epidurally nucleus pulposus such as sequestered type herniated intervertebral disc and transligamentous extrusion type herniated intervertebral disc, comprising glycosaminoglycan degrading enzyme as an active ingredient. The same explanation as described above for the composition of the present invention shall apply to the glycosaminoglycan degrading enzyme that can be used as the active ingredient in the therapeutic agent of the present invention, the content of the active ingredient, the pharmaceutical carriers to be contained, the subject to be treated, the part to be treated, the dose, and the like.

The composition and the therapeutic agent of the present invention function to quickly and considerably dissolve nucleus pulposus in the vertebral epidural space in the case of epidurally migrating herniated intervertebral disc and enhance phagocytosis of nucleus pulposus by phagocytes, thereby enabling quick remission of serious pain accompanying with epidurally migrating herniated intervertebral disc. Further, the composition and the therapeutic agent are highly useful as safe medicines since they do not affect spinal cord at all.

BRIEF DESCRIPTION OF THE DRAWING

FIG. 1 shows the contents of each glycosaminoglycan in fluorescence-labeled nucleus pulposus in the vertebral epidural space when chondroitinase ABC was administered to the vertebral epidural space.

DETAILED DESCRIPTION OF THE PREFERRED EMBODIMENT

The following Examples will be illustrated below in detail as Test Examples and Preparation Examples, but are not construed to limit the technical scope of the present invention.

TEST EXAMPLE (1) Acute Toxicity Test

Glycosaminoglycan degrading enzyme (chondroitinase ABC (Seikagaku Corporation) was used herein; hereinafter sometimes referred simply to as CABC) was subjected to the acute toxicity test.

1) Acute Toxicity Test Using Rats

Chondroitinase ABC was intravenously administered once to five male and five female rats in a dose of 2,000 U/kg. For 14 days after the administration, the rats were observed for their general sign and survival and were weighed. After 14 days, the rats were subjected to autopsy, and their main organs were macroscopically observed.

As a result, no animal died and no change was observed for general sign, the body weight, and finding in autopsy. Thus, the no adverse level of chondroitinase ABC by intravenous administration to rats is estimated as 2,000 U/kg.

2) Acute Toxicity Test Using Beagles

Chondroitinase ABC was administered once to the epidural space of the vertebral canal of two male and two female beagles in a dose of 40 U/animal. For 4 weeks after the administration, the dogs were observed for their general sign and survival and were weighed. After 4 weeks, the beagles were subjected to autopsy, and their main organs were macroscopically observed.

As a result, no animal died and no change was observed for general sign, the body weight, and finding in autopsy. Thus, the no adverse level of chondroitinase ABC by administration to the epidural space of dogs is estimated as 40 U/kg.

(2) Pharmacological Test for Pharmaceutical Effect

Study of the effect of glycosaminoglycan degrading enzyme on enhancement of disappearance of nucleus pulposus migrating in the vertebral epidural space The effect of glycosaminoglycan degrading enzyme on enhancement of disappearance of nucleus pulposus migrating in the vertebral epidural space was studied using a rabbit by transplanting nucleus pulposus labeled with fluorescence into the epidural space of the rabbit, administering glycosaminoglycan degrading enzyme to the vertebral epidural space, and determining the change in the amount of glycosaminoglycan in the transplanted fluorescence-labeled nucleus pulposus. In this experiment, a decrease in the amount of glycosaminoglycan in the transplanted fluorescence-labeled nucleus pulposus means enhancement of disappearance of nucleus pulposus.

(2-1) Test Scheme

After preparing the fluorescence-labeled nucleus pulposus, about 50 mg of it was transplanted into the vertebral epidural space of a rabbit. Immediately thereafter, 2 ml of 25 U/ml of glycosaminoglycan degrading enzyme, which was chondroitinase ABC herein, was administered to the vertebral epidural space of the rabbit. On the next day, the rabbit was sacrificed and the fluorescence-labeled nucleus pulposus was collected to measure the amount of glycosaminoglycan in the collected fluorescence-labeled nucleus pulposus.

(2-2) Materials (2-2-1) Animal

A normal JW female rabbit weighing about 3 kg was used as an animal for collecting the nucleus pulposus referred to as nucleus pulposus-donor animal.

A normal JW female rabbit weighing about 3 kg was used as an animal into which the nucleus pulposus is transplanted referred to as nucleus pulposus-recipient animal.

(2-2-2) Test Substance

The following test substance were all aseptic.

Phosphate-buffered saline (PBS) was used as negative control.

As the test substance including glycosaminoglycan degrading enzyme, a mixed solution of 0.5 mL of chondroitinase ABC (Seikagaku Corporation; 1,000 U/rnL) and 10 mL of phosphate-buffered saline was used.

(2-3) Group Constitution of Nucleus Pulposus-recipient Animals

The group constitution used in this test is shown in Table 1.

TABLE 1

| Group | Test substance | Dose | Number of animals |
|---|---|---|---|
| control substance-administered group | PBS | 2 mL/animal | 5 |
| CABC-administered group | 47.6 U/mL CABC | 2 mL/animal | 6 |

(2-4) Preparation of Fluorescence-labeled Nucleus Pulposus

The following procedures were carried out aseptically.

Intervertebral discs of L6/L7, L5/L6, L4/L5, L3/L4, and L2/L3 were taken out from nucleus pulposus donor animal (rabbit). Nucleus pulposus was collected and pooled in a 50-mL centrifuge tube. A 10 $\mu$L portion of a 50 mg/mL N,N-dimethylformamide (DMF) solution of fluorescein isothiocyanate (FITC) was added to the 50-mL centrifuge tube containing nucleus pulposus and mixed. This centrifuge tube was allowed to stand at 0° C. for 5 days in a dark room. On day 6, nucleus pulposus in the centrifuge tube was divided in 50-mg portions and each portion was put into a tube containing phosphate-buffered saline. The tubes were centrifuged for washing of nucleus pulposus. The thus-obtained nucleus pulposus was referred to as "fluorescence-labeled nucleus pulposus".

The fluorescence-labeled nucleus pulposus was used to transplant to 5 animals in the control substance-administered group and 6 animals in the CABC-administered group.

(2-5) Transplantation of Fluorescence-labeled Nucleus Pulposus into Vertebral Epidural Space The fluorescence-labeled nucleus pulposus was transplanted into the vertebral epidural space under inhalation anesthesia with Halothane (trade name; Takeda Chemical Industries). The hair-cut part on the back through the tail of the nucleus pulposus-recipient animals was disinfected with ethanol and Isozin (trade name; Meiji Seika) and then fixed. The skin on the back was cut by about 4 cm with a scalpel and dissected. Spinous process and vertebral arch were removed and yellow ligament between L5 and L6 was vertically dissected. With making space using a spartale, 50 mg of the fluorescence-labeled nucleus pulposus was transplanted into th e tail side. The fluorescence-labeled nucleus pulposus was transplanted into the vertebral epidural space of L6. After transplantation, the dissected site was sutured.

(2-6) Administration of Test Substance

In order to administer the test substance, the skin in the vicinity of L6/L7 intervertebral disc at the tail side from the fluorescence-labeled nucleus pulposus-transplanted site was dissected. The test substance was administered into the vertebral epidural space from L6/L7 intervertebral disc at the tail side from the fluorescence-labeled nucleus pulposus-transplanted site at a rate of 0.5 mL/min using an infusion pump. After completion of administration, the dissected site was sutured and disinfected with Isozin (trade name; Meiji Seika).

(2-7) Recovery of Transplanted Fluorescence-labeled Nucleus Pulposus

On the next day, the nucleus pulposus recipient animals were sacrificed by exsanguination. The part from vertebrae lumbales L2 to cauda equina was excised and vertebral canal was exposed from the abdominal side. Then, the fluorescence-labeled nucleus pulposus was recovered from the embedded part under the spinal cord.

(2-8) Quantification of Glycosaminoglycan in Fluorescence-labeled Nucleus Pulposus (2-8-1) Lyophilization The recovered fluorescence-labeled nucleus pulposus was lyophilized. After completion of lyophilization, the lyophilizate was weighed. The weighed samples were transferred to another tube.

(2-8-2) Digestion with Actinase

A 1 mL portion of a 0.25% actinase solution was added thereto to effect digestion at 55° C. for about 3 hours and a half. After the digestion, the reaction mixture was heat-treated at 100° C. for 10 minutes to deactivate actinase. Thus, a solution of actinase-digested fluorescence-labeled nucleus pulposus was obtained.

(2-8-3) Digestion with Glycosaminoglycan Lyase

In order to quantify various glycosaminoglycans, namely chondroitin sulfate, keratan sulfate, and hyaluronan, in the fluorescence-labeled nucleus pulposus, the solution of actinase-digested fluorescence-labeled nucleus pulposus was digested with the following glycosaminoglycan lyase.

(2-8-3-1) Digestion with Chondroitinase A 100 $\mu$L portion of the solution of actinase-digested fluorescence-labeled nucleus pulposus was put into a tube. Then, 20 $\mu$L of 5 U/mL chondroitinase ABC (Seikagaku Corporation) was added thereto. The digestion reaction was carried out at 37° C. for 2 hours under slightly stirring. After completion of the digestion, 20 $\mu$L of 5 U/mL chondroitinase AC-II (Seikagaku Corporation) and 20 $\mu$L of 1M sodium acetate buffer (pH 6.0) were added to the reaction mixture. The digestion reaction was carried out again at 37° C. for 2 hours under slightly stirring to obtain chondroitinase-digested product of the fluorescence-labeled nucleus pulposus. This digestion product was used as a sample for quantification of chondroitin sulfate and hyaluronan in the fluorescence-labeled nucleus pulposus.

Chondroitin sulfate in the fluorescence-labeled nucleus pulposus can be quantified by detecting $\Delta$Di-6S which represents 2-acetamido-2-deoxy-3-O-($\beta$-D-gluco-4-enopyranosyluronic acid)-6-O-sulfo-D-galactose, $\Delta$Di-4S which represents 2-acetamido-2-deoxy-3-O-($\beta$-D-gluco-4-enopyranosyluronic acid)-4-O-sulfo-D-galactose, and $\Delta$D i-0S which represents 2-acetamido-2-deoxy-3-O-($\beta$-D-gluco-4-enopyranosyluronic acid)-D-galactose, derived from chondroitin sulfate contained in this digested product, by high-performance liquid chromatography as described later. On the other hand, hyaluronan in the fluorescence-labeled nucleus pulposus can be quantified by detecting $\Delta$Di-HA which represents 2-acetamido-2-deoxy-3-O-($\beta$-D-gluco-4-enopyranosyluronic acid)-D-glucose, derived from hyaluronan contained in this digested product, by high-performance liquid chromatography as described later.

(2-8-3-2) Digestion with Keratanase

A 100 $\mu$L portion of the solution of the fluorescence-labeled nucleus pulposus digested with actinase was put into a tube. Then, 20 $\mu$L of 0.1 U/mL keratanase prepared by the method described in WO96/16166 and 20 $\mu$L of 1M sodium acetate buffer (pH 6.0) were added thereto. The digestion was performed at 37° C. for 48 hours under slightly stirring to obtain the digestion product of the fluorescence-labeled nucleus pulposus with keratanase. This digestion product was used as a sample for quantification of keratan sulfate in the fluorescence-labeled nucleus pulposus.

Keratan sulfate in the fluorescence-labeled nucleus pulposus can be quantified by detecting Gal-GlcNAc(6S) (hereinafter sometimes referred to as L2) and Gal(6S)-GlcNAc(6S) (hereinafter sometimes referred to as L4), wherein Gal represents a galactose residue, GlcNAc represents an N-acetylglucosamine residue, (6S) represents 6-O-sulfate ester, and—represents a glycoside bond, derived from keratan sulfate contained in the digestion product by high-performance liquid chromatography as described later.

(2-8-4) Ultrafiltration

After digestion with glycosaminoglycan lyase, the whole amount of each digestion product was subjected to ultrafiltration using centrifuge ultrafiltration tube with molecular weight cutoff of 10,000 (trade name: Ultrafree, Millipore).

(2-8-5) High-performance Liquid Chromatography (HPLC)

A 5 to 10 $\mu$L portion of the filtrate resulted from the above ultrafiltration was applied onto the HPLC column. The HPLC conditions for analysis of $\Delta$Di-6S, $\Delta$Di-4S, and L4 are described below.

(1) Column: Senshu Pack N(CH$_3$) 2-315-N, $\phi$8 mm×15 cm (Senshu Kagaku);
(2) Elution: 20 mM Na$_2$SO$_4$/acetonitrile=9/1;
(3) Flow rate: 0.65 mL/min;
(4) Reaction mixture: 50 mM sodium tetraborate containing 0.1% 2-cyano-acetamide;
(5) Flow rate of reaction mixture: 0.65 mL/min;
(6) Reaction temperature: 150° C.;
(7) Reaction coil: $\phi$0.4 mm×10 m; and
(8) Detection: excitation wavelength of 331 nm, emission wavelength of 383 nm.

The HPLC conditions for analysis of $\Delta$Di-HA, $\Delta$Di-OS, and L2 are described below.

(1) Column: Asahi Pack NH2P, $\phi$4.6 mm×25 cm×2 columns (Asahi Chemical Industry);
(2) Elution: 25 mM tetramethylammonium-acetic acid buffer (pH 8.5)/acetonitrile=9/1;
(3) Flow rate: 0.5 mL/min
(4) Reaction mixture: 50 mM sodium tetraborate containing 0.1% 2-cyano-acetamide;
(5) Flow rate of reaction mixture: 0.5 mL/min;
(6) Reaction temperature: 150° C.;
(7) Reaction coil: $\phi$0.4 mm×10 m; and
(8) Detection: excitation wavelength of 331 nm, emission wavelength of 383 nm.

FIG. 1 shows the content of ΔDi-HA, which is an index for the content of hyaluronan, ΔDi-CS showing the total content of ΔDi-6S, ΔDi-4S, and ΔDi-0S, which is an index for the content of chondroitin sulfate, and Di-KS showing the total content of L2 and L4, which is an index of the content of keratan sulfate, in the fluorescence-labeled nucleus pulposus in the control substance-administered group and the CABC-administered group. In FIG. 1, PBS represents for the control substance-administered group, and C-ABC for the CABC-administered group. Further, in FIG. 1, HA, CS, and KS represent hyaluronan, chondroitin sulfate, and keratan sulfate, respectively. ** means that there is a significant difference with $p<0.05$ and * means there is a significant difference with $p<0.1$, between the two groups as a result of the t-test.

As a result, the contents of any glycosaminoglycan in the transplanted fluorescence-labeled nucleus pulposus in the CABC-administered group was remarkably reduced as compared with those in the control substance-administered group. Particularly, there was statistically significant decrease in the contents of chondroitin sulfate and keratan sulfate in the transplanted fluorescence-labeled nucleus pulposus in the CABC-administered group as compared with those in the control substance-administered group.

Further, as a result of histological observation, infiltration of phagocyte was observed in a shorter period of time in the CABC-administered group as compared with the control substance-administered group. A number of granulocytes and macrophages also infiltrated in the CABC-administered group. Phagocytosis of epidurally migrating nucleus pulposus by these phagocytes took place. It was indicated that administration of CABC also enhances phagocytosis of epidurally migrating nucleus pulposus by phagocytes.

As a result of further observation, CABC did not affect spinal cord at all.

This result revealed that CABC administered in the vertebral epidural space not only functions to extremely efficiently digest nucleus pulposus in the vertebral epidural space but also enhances phagocytosis of epidurally migrating nucleus pulposus by phagocytes to extremely efficiently eliminate epidurally migrating nucleus pulposus. It was also indicated that CABC digested only nucleus pulposus in the vertebral epidural space without making any influence on spinal cord.

From the above results, it was found that the composition for administration to vertebral epidural space comprising a glycosaminoglycan degrading enzyme and the therapeutic agent for epidurally migrating herniated intervertebral disc comprising a glycosaminoglycan degrading enzyme as an active ingredient have the effect to extremely efficiently and effectively eliminating epidurally migrating nucleus pulposus without affecting spinal cord by not only efficiently digesting nucleus pulposus of herniated intervertebral disc migrating in the vertebral epidural space but also enhancing phagocytosis of nucleus pulposus by phagocytes.

PREPARATION EXAMPLE

1) A mixture of 0.5 mL of chondroitinase ABC (Seikagaku Corporation; 1,000 U/mL) and 10 mL of phosphate-buffered saline was filter sterilized and distributed into ampules in 2 mL portions. The ampules were sealed. Thus, injectable preparations for treatment of epidurally migrating herniated intervertebral disc were produced.

2) Keratanase II which is Keratan sulfate endo-β-N-acetylglucosaminidase (Seikagaku Corporation) (final concentration of 20 U/mL), saccharose (final concentration of 1% (w/w)), and polyethylene glycol 4000 (final concentration of 2% (w/w)) were dissolved in 10 mM phosphate buffer (pH 7.0). The mixture was distributed in 0.5 mL portions/vial and lyophilized. The lyophilization was carried out by cooling from room temperature to −45° C. for freezing, effecting first drying for 12 hours under reduced pressure at 60 mTorr, raising the temperature up to 25° C. with 12 hours, and effecting second drying at 25° C. for 10 hours. After drying, the vials were pressured with nitrogen gas and plugged. Thus, the injectable lyophilized composition for administration to the vertebral epidural space were produced.

What is claimed is:

1. A method for treating epidurally-migrating herniated intervertebral disc wherein nucleus pulposus migrates into a vertebral epidural space, which comprises the step of administering a glycosaminoglycan-degrading enzyme to a vertebral epidural space of a mammal in need thereof until nucleus pulposus within the vertebral epidural space is dissolved by digestion by the enzyme and by facilitation of emersion and infiltration of phagocytes.

2. The method according to claim 1, wherein said herniated intervertebral disc is sequestered type herniated intervertebral disc.

3. The method according to claim 1, wherein said herniated intervertebral disc is transligamentous extrusion type herniated intervertebral disc.

4. The method according to claim 1, wherein said mammal is a human.

5. The method according to claim 1, wherein said glycosaminoglycan degrading enzyme is chondroitinase.

6. The method according to claim 5, wherein said chondroitinase is chondroitinase ABC.

7. The method according to claim 1, wherein said enzyme is administrated in an amount of more than 5 units.

8. A method for treating epidurally-migrating herniated intervertebral disc wherein nucleus pulposus migrates into a vertebral epidural space, which comprises the step of administrating a glycosaminoglycan-degrading enzyme to a vertebral epidural space of a mammal in need thereof in an amount effective to facilitate emersion and infiltration of phagocytes into nucleus pulposus within the vertebral epidural space.

9. The method according to claim 8, wherein said mammal is a human.

10. The method according to claim 8, wherein said glycosaminoglycan-degrading enzyme is chondroitinase.

11. The method according to claim 10, wherein said chondroitinase is chondroitinase ABC.

12. A method for facilitating infiltration of phagocytes into nucleus pulposus within a vertebral epidural space of a mammal, which comprises the step of administrating an effective amount of a glycosaminoglycan-degrading enzyme to the vertebral epidural space until emersion and infiltration of phagocytes into nucleus pulposus within the vertebral epidural space are facilitated.

13. The method according to claim 12, wherein said mammal is a human.

14. The method according to claim 12, wherein said glycosaminoglycan-degrading enzyme is chondroitinase.

15. The method according to claim 14, wherein said chondroitinase is chondroitinase ABC.

* * * * *